United States Patent [19]

Drent et al.

[11] Patent Number: 5,414,109
[45] Date of Patent: May 9, 1995

[54] PROCESS FOR THE CARBONYLATION OF ACETYLENICALLY UNSATURATED COMPOUNDS

[75] Inventors: Eit Drent; Eric Kragtwijk, both of Amsterdam, Netherlands

[73] Assignee: Shell Oil Company, Houston, Tex.

[21] Appl. No.: 198,918

[22] Filed: Feb. 18, 1994

[30] Foreign Application Priority Data

Mar. 19, 1993 [EP] European Pat. Off. ........... 93200821

[51] Int. Cl.$^6$ ................................................ C07C 67/36
[52] U.S. Cl. ...................................... 560/207; 560/97
[58] Field of Search ...................................... 560/207, 97

[56] References Cited

U.S. PATENT DOCUMENTS

| | | | |
|---|---|---|---|
| 4,668,816 | 5/1987 | Epstein | 560/207 |
| 4,739,109 | 4/1988 | Drent | 560/207 |
| 4,739,110 | 4/1988 | Drent | 560/207 |
| 4,789,756 | 12/1988 | Drent | 560/104 |
| 4,831,187 | 5/1989 | Drent | 560/207 |
| 4,940,787 | 7/1990 | Drent | 536/124 |
| 5,028,576 | 7/1991 | Drent et al. | 502/167 |
| 5,028,734 | 7/1991 | Drent | 560/207 |
| 5,099,062 | 3/1992 | Drent et al. | 560/207 |
| 5,103,048 | 4/1992 | Drent et al. | 56/207 |
| 5,149,868 | 9/1992 | Drent | 562/497 |
| 5,158,921 | 10/1992 | Drent et al. | 502/167 |
| 5,166,411 | 11/1992 | Drent | 560/207 |
| 5,177,253 | 1/1993 | Drent et al. | 560/207 |
| 5,179,225 | 1/1993 | Drent et al. | 560/207 |
| 5,189,003 | 2/1993 | Klusener et al. | 502/167 |
| 5,258,546 | 11/1993 | Klusener et al. | 560/207 |

FOREIGN PATENT DOCUMENTS

| | | |
|---|---|---|
| 0186228A1 | 7/1986 | European Pat. Off. . |
| 0386833A1 | 9/1990 | European Pat. Off. . |
| 0386834A1 | 9/1990 | European Pat. Off. . |
| 0441446A1 | 8/1991 | European Pat. Off. . |
| 0441447A1 | 8/1991 | European Pat. Off. . |
| 565199 | 10/1993 | European Pat. Off. . |
| 0565199A2 | 10/1993 | European Pat. Off. . |
| 2202165 | 9/1988 | United Kingdom . |

*Primary Examiner*—Paul J. Killos

[57] ABSTRACT

A process for the carbonylation of acetylenically unsaturated compounds in the presence of a nucleophilic compound having one or more removable hydrogen atoms and a catalyst system based on a source of platinum, a bisphosphine of the formula $R_1R_2PRPR_3R_4$ wherein each of $R_1, R_2, R_3$ and $R_4$ independently represents a hydrocarbyl group and R represents a bivalent bridging group and a source of anions from a conjugated base of an acid having a pKa of less than 4.

20 Claims, No Drawings

PROCESS FOR THE CARBONYLATION OF ACETYLENICALLY UNSATURATED COMPOUNDS

BACKGROUND OF THE INVENTION

The invention relates to a process for the carbonylation of acetylenically unsaturated compounds.

The invention is of particular interest for the preparation of esters of unsaturated carboxylic acids such as acrylic acid and methacrylic acid. It is well known that the alkyl esters of these acids, in particular the methyl and butyl esters, are of great commercial importance.

The general preparation of esters of unsaturated acids by carbonylation of acetylenically unsaturated compounds is known. In EP-186228, for example, a process for the carbonylation of acetylenically unsaturated compounds is described in which a catalyst system comprising a palladium compound, a phosphine and a protonic acid are used. The examples illustrate the use of, optionally substituted, hydrocarbylphosphines such as (substituted) triphenylphosphine. These phosphines are used in relatively large amounts, i.e. 5 to 500 moles per gramatom of palladium.

Another process for the carbonylation of acetylenically or olefinically unsaturated compounds is disclosed in EP 441.446. In this process, esters of unsaturated acids are prepared using a catalyst system which comprises a source of a Group VIII metal, a phosphine having an aromatic substituent which contains an imino nitrogen atom, a protonic acid and a tertiary amine. All examples relate to the use of catalyst systems containing palladium and a pyridylphosphine ligand.

Some in the art have investigated whether the carbonylation of unsaturated compounds is restricted to the use of palladium containing catalysts or whether satisfactory conversions and yields can be obtained with a catalyst comprised of a Group VIII metal other than palladium. GB 2202165 describes a process in which ethene, acrylic acid, or an acrylate ester is reacted with carbon monoxide in the presence of hydrogen, using a catalyst system formed by combining a platinum (II) compound, an organic ligand containing at least two phosphorus atoms coordinating with the platinum atom and a protonic acid having a pKa below 3. As unsaturated starting materials only ethene, acrylic acid and acrylic esters are mentioned. However, in this process the predominant reaction product is not an ester but a ketone.

SUMMARY OF THE INVENTION

It is an object of this invention to provide a process for the carbonylation of acetylenically unsaturated compounds.

It is a further object of this invention to provide a catalyst system for the carbonylation of acetylenically unsaturated compounds.

It is a yet further object of this invention to provide an improved process for the carbonylation of acetylenically unsaturated compounds using a platinum based catalyst system.

In accordance with this invention a process for the carbonylation of acetylenically unsaturated compounds is provided. The process is conducted in the presence of a nucleophilic compound having at least one removable hydrogen atoms and a catalyst system having:

(a) a source of platinum (b) a bisphosphine of the formula $R_1R_2PRPR_3R_4$ (Formula I) wherein $R_1, R_2, R_3$ and $R_4$ independently are hydrocarbyl groups and hydrocarbyl groups substituted with halogen atoms, cyano, alkoxy, acyl, alkylamino or dialkylamino groups, R is a bivalent bridging group containing 2 to 5 atoms in the bridge; and (c) a source of anions which is the conjugated base of an acid with a pKa of less than 4.

DETAILED DESCRIPTION OF THE INVENTION

Surprisingly, it has now been found that by selecting an acetylenically unsaturated compound as starting material, platinum containing catalysts can be used for preparing esters of unsaturated carboxylic acids. Furthermore, diolefinic by-products can be formed in good yields which, owing to the presence of two double bonds, are suitable intermediates for the preparation of various commercially useful products.

The catalyst systems of the invention employ a source of platinum which is capable of complexing with the two phosphorus atoms of the bisphosphine of formula (I). Suitable compounds include, but are not limited to, platinum (II) salts, such as potassium tetracyanoplatinate, sodium tetracyanoplatinate, potassium trichloro (ethylene) platinate (II), platinum-bis(cyanobenzene)disulphate, potassium tetrachloroplatinate (II), platinum bis (tri phenylphosphine) disulphate and potassium trichloro(ethylene) platinate (II). Salts of platinum with carboxylic acids, in particular with carboxylic acids having up to 12 carbon atoms, e.g. acetic acid, are also suitable.

Preferred sources of platinum are organic platinum (II) complexes. Platinum (II)acetylacetonate is the most preferred source of platinum.

In the bisphosphines of formula (I), it is prefered that each of $R_1, R_2, R_3$, and $R_4$ is, independently, an aryl group. These aryl groups may be unsubstituted or may be substituted with one of more substituents selected from the group consisting of halogen atoms and alkoxy groups containing from 1 to 4 carbon atoms. Suitable aryl groups include, but are not limited to, substituted and non substituted naphthyl-,and phenyl- groups. Examples of such suitable aryl groups include are phenyl-, p-tolyl-, p-methoxyphenyl- and p-chlorophenyl groups. $R_1, R_2, R_3$ and $R_4$ may represent different groups, but preferably are the same.

The bivalent bridging group in the bisphosphines of formula (I), represented by R, preferably contains from 2 to 4 atoms in the bridge. A bridging group having 3 atoms is particularly preferred. The bridging atoms are preferably all carbon atoms but bridging groups containing a carbon chain interrupted by a hetero atom, such as an oxygen atom, are also suitable. Examples of suitable bisphosphines are 1,2-bis (diphenyl- phosphino) ethane, 1,2-bis (diphenylphosphino) ethene, 1,3-bis (diphenylphosphino) propane, 1,3-bis (diethylphosphino) propane, 1,4-bis (diphenylphosphino) butane, 1,3-bis (di-isopropylphosphino) propane and 1,3-bis (di-p-methoxyphenyl phosphino) propane. 1,3-Bis (diphenylphosphino) propane is particularly preferred.

Any compound that can generated anions can generally be used as the anion source of the catalyst system of this invention. Preferably the anion is a non-coordinating or substantially non-coordinating anion, which, in the context of the present specification, means that little or no co-valent interaction occurs between the anion and the platinum in the catalyst. Preferred anion sources are the acids, of which the anions are the conjugated base. The acids have a pKa of less than 4 (measured in aqueous solution at 18° C.) and preferably less than 2. Other suitable anion sources are salts of these acids. Metal salts containing a non-noble transition metal, such as zirconium, vanadium, chromium, manganese, cobalt, nickel and iron (II) can be used in this capacity.

Typical examples of suitable anions in the catalyst system of the invention, are anions of phosphoric acid, phosphonic acid, sulphuric acid, sulphonic acids and trihaloacetic acid. Sulphonic acids such as methanesulphonic acid, trifluoromethanesulphonic acid and p-toluenesulphonic acid are preferred anion sources. Alkylsulphonic acids are particularly preferred. tert.butylsulphonic acid is most preferred.

In contrast to the process described in EP-186228, the process according to the invention employs a molar amount of bisphosphine that is relatively small compared to the amount of noble metal of Group VIII of the Periodic table. A molar excess of bisphosphine is advantageous.

Preferably, between about 0.5 and 10 moles of bisphosphine of formula (I) are used per gramatom of platinum. It is particularly preferred that the range be between 0.7 and 3 moles of bisphosphine per gramatom of platinum.

The amount of platinum (II) is not critical. Usually catalytic amounts of platinum compounds are applied, whereby the quantity of platinum is preferably in the range of $10^{-6}$ to $10^{-1}$ gramatom of platinum per mole of acetylenically unsaturated compound.

The acetylenically unsaturated compound is usually a linear alkyne having from 2 to 20 carbon atoms. If desired, the compound may be sustituted with one or more inert substituents such as halogen atoms or hydroxy groups. The acetylenically unsaturated bond is, as a rule, the only carbon-carbon unsaturation in the molecule and is preferably located at a terminal position. Examples of suitable acetylenically unsaturated compounds are acetylene, propyne, 1-butyne, 2-butyne, 1-pentyne, phenylacetylene, 3-chlorobutyne, 4-hydroxypentyne and 1-nonyne. Acetylene and propyne are particularly preferred starting materials.

Without wishing to be bound by any specific reaction mechanism, it is believed that in the carbonylation process of the invention, the overall reaction can best be indicated by the following equation:

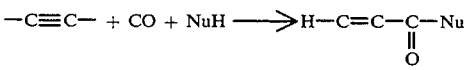

Equation (I)

wherein Nu represents the nucleophilic moiety of the nucleophilic co-reactant after removal of a hydrogen atom.

As evident from equation (I), the obtained reaction product largely depends on the nature of the nucleophilic compound, represented by NuH. Thus, if NuH represents a carboxylic acid, the resulting product will contain an anhydride moiety, if NuH represents water the product will be an acid and if NuH represents an alcohol, an ester will be formed.

The carbonylation reaction of the invention is preferably carried out with an alcohol as nucleophilic compound. Suitable alcohols include mono alcohols having between 1 and 12 carbon atoms, in particular from 1 to 6 carbon atoms and dihydric alcohols having from 2 to 8 carbon atoms. It will be appreciated that in a reaction in which a nucleophilic compound participates, from which two hydrogen atoms can be removed, other reaction products can be formed such as glycolesters.

Examples of suitable alcohols are methanol, ethanol, n-propanol, iso-propanol, butanol-1, butanediol-1,4, cyclohexanol, and ethyleneglycol. Lower monohydric alcohols having from 1 to 4 carbon atoms are preferred. Methanol and 1-butanol are particularly preferred.

The reaction may be carried out in the presence of a separate diluent, if so desired. Preferred diluents are aprotic liquids such as ketones and ethers. The use of the dimethylether of ethylene glycol (diglyme) has given particularly attractive results.

A reaction between two molecules of the acetylenically unsaturated compound, carbon monoxide and the nucleophilic co-reactant may take place to form a diolefinic reaction product due to the reactivity of acetylenically unsaturated compounds, in addition to the carbonylation reaction, indicated by the equation (I).

This reaction may be represented by the equation:

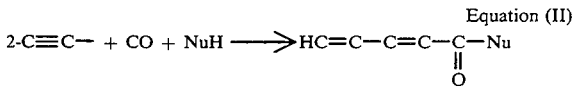

Equation (II)

The formation of the diolefinic compound may be enhanced or suppressed by modifying the reaction conditions such as temperature, pressure and acidity of the reaction medium.

Suitable reaction temperatures are usually between about 30° and 250° C., preferably between about 50° and 200° C. and more preferably between 70° and 140° C. The reaction pressure is preferably between 20 and 80 bar. Higher pressures are generally not recommended because of difficulties presented in properly running the reactor under these conditions.

The invention is further illustrated with the following examples.

EXAMPLES I-X

A solution of 0.2 mmol of platinum (II) acetylacetonate in 40 mL of diglyme (2,5,8-trioxanonane), also containing bisphosphine, anion source and nucleophilic co-reactant in the amounts, as specified below, were introduced into a 250 mL "Hastelloy C" (Trade Mark) autoclave, provided with a magnetic stirrer.

The reactor was closed and the gaseous acetylenically unsaturated compound and subsequently carbon monoxide (20 bar) was added. (In Examples VIII and IX phenylacetylene was introduced in the reactor together with the catalyst solution.) The contents of the autoclave were then heated under stirring to the desired reaction temperature, indicated in the Table and maintained at that temperature during the reaction period (1-5 hour). After completion of the reaction, the reaction mixture was cooled to room temperature. The product was analysed by means of high performance liquid chromatography.

The analytical results, viz. the average rate in moles of product per gramatom of platinum and per hour, the selectivity with respect to the desired ester and the co-formed byproducts, are shown in the Table.

The abbreviations used in the Table, have the following meanings:

PA = platinum (II) acetylacetonate

BDPP = 1,3 - bis (diphenylphosphino) propane
BDPB = 1,4 - bis (diphenylphosphino) butane
BEPP = 1,3 - bis (diethylphosphino) propane
BCPP = 1,3 - bis (di-2-cyanoethylphosphino) propane
BIPP = 1,3 - bis (di-isopropylphosphino) propane
TBSA = tertiary butylsulphonic acid
TFA = trifluoro acetic acid
BA = butylacrylate
AA = acrylic acid
1-BPA = butylester of 1-phenylacrylic acid
2-BPA = butylester of 2-phenylacrylic acid
MMA = methylmethacrylate
MCA = methylcrotonate
BPD = butylpentadienoate
MDPD = methylester of 2,4-dimethyl pentadienoic acid.
DBA = dibutylacetal
PDA = pentadienoic acid.

TABLE

| Example No. | Catalyst Components (mmol) Pt source | bisphosphine | anion source | Acetylenically unsat. compound | Nucleophil co-reactant mL | Temp. °C. | Average rate mol/gat Pt.h | Products (1) sel % | (2) |
|---|---|---|---|---|---|---|---|---|---|
| I | 0.2 PA | 0.22 BDPP | 0.4 TBSA | Ethyne, 1.4 bar | 15 butanol | 100 | 125 | BA 92 | BPD |
| II | 0.2 PA | 0.22 BDPP | 0.4 TBSA | Ethyne, 1.4 bar | 30 butanol | 125 | 200 | BA 91 | " |
| III | 0.2 PA | 0.22 BDPB | 0.4 TBSA | Ethyne, 1.4 bar | 30 butanol | 100 | 50 | BA 90 | " |
| IV | 0.2 PA | 0.22 BEPP | 0.4 TBSA | Ethyne, 1.4 bar | 30 butanol | 100 | 50 | BA 60 | BPD + DBA |
| V | 0.2 PA | 0.2 BCPP | 0.4 TBSA | Ethyne, 1.4 bar | 30 butanol | 100 | 20 | BA 60 | BCD + DBA |
| VI | 0.2 PA | 0.2 BDPP | 0.5 TFA | Ethyne, 1.4 bar | 30 butanol | 100 | 120 | BA 70 | BPD, 25 |
| VII | 0.2 PA | 0.2 BDPP | 0.4 TBSA | Ethyne, 1.4 bar | 2 water | 100 | 150 | BA 91 | PDA |
| VIII | 0.2 PA | 0.2 BDPP | 0.4 TBSA | phenylethyne 15 mL | 30 butanol | 125 | 120 | (95) 1-BPA (5) 2-BPA | 95 |
| IX | 0.2 PA | 0.2 BIPP | 0.4 TBSA | phenylethyne 15 mL | 10 methanol | 125 | 30 | (90) 1-BPA (10) 2-BPA | 90 |
| X | 0.2 PA | 0.2 BDPP | 0.4 TBSA | propyne 15 mL | 10 methanol | 125 | 120 | (94) MMA (5) MCA | MDPP 95 |

(1) Mono unsaturated ester
(2) Diunsaturated ester, acetal

Comparison of the results of Examples I and III supports the preference for bisphosphines in which the phosphorus atoms are separated by a trimethylene group instead of a tetramethylene group.

Similarly, the preference for bis-diarylphosphines over bis-dialkylphosphine is supported by comparing the results of Examples IV and V with those of Example I and by comparing the results of Example IX with those of Example VIII.

While this invention has been described in detail for the purpose of illustration, it is not to be construed or limited thereby but is intended to cover all changes and modifications within the spirit and scope thereof.

What is claimed is:

1. A process for the carbonylation of acetylenically unsaturated compounds in the presence of a nucleophilic compound having at least one removable hydrogen atoms and a catalyst system comprising:
   (a) a source of platinum
   (b) a bisphosphine of the formula $R_1R_2PRPR_3R_4$ (I) wherein $R_1, R_2, R_3$ and $R_4$ independently are selected from the group consisting of unsubstituted hydrocarbyl groups and hydrocarbyl groups substituted with substituents selected from the group consisting of halogen atoms, cyano, alkoxy, acyl, alkylamino and dialkylamino groups, R is a bivalent bridging group containing 2 to 5 atoms in the bridge; and
   (c) a source of anions being the conjugated base of an acid having a pKa of less than 4.

2. A process as claimed in claim 1, wherein said platinum source is an organic platinum complex.

3. A process as claimed in claim 1 wherein said platinum source is a platinum (II) acetylacetonate.

4. A process as claimed in claim 1 wherein $R_1, R_2, R_3$ and $R_4$ are independently selected from the group consisting of unsubstituted aryl groups and aryl groups substituted with substituents selected from the group consisting of halogen atoms and alkoxy groups containing from 1 to 4 carbon atoms; and R contains 3 carbon atoms in the bridge.

5. A process as claimed in claim 4 wherein said biphosphine is 1,3-bis (diphenylphosphino) propane.

6. A process as claimed in claim 1 wherein said source of anions comprises a sulphonic acid.

7. A process as claimed in claim 6 wherein said sulphonic acid is an alkylsulphonic acid.

8. A process as claimed in claim 7 wherein said alkylsulphonic acid is tertiary butylsulphonic acid.

9. A process as claimed in claim 1 wherein said bisphosphine comprises between about 0.5 and 10 moles per gram atom of platinum.

10. A process as claimed in claim 9 wherein said comprises between about 0.7 and 3 moles per gram atom of platinum.

11. A process as claimed in claim 1 wherein platinum comprises between about $10^{-6}$ and $10^{-1}$ gram atoms per mole of acetylenically unsaturated compound.

12. A process as claimed in claim 1 wherein said acetylenically unsaturated compound is selected from the group consisting of acetylene and propyne.

13. A process as claimed in claim 1 wherein said nucleophilic compound having one of more removable hydrogen atoms is a $C_{1-6}$ alcohol.

14. A process as claimed in claim 13 wherein said alcohol is butanol.

15. A process as claimed in claim 1 wherein the reaction is carried out at a temperature between about 50° and 200° C.

16. A process as claimed in claim 15 wherein the reaction is carried out at a temperature between about 70° and 140° C.

17. A process as claimed in claim 1 wherein the reaction is carried out at a pressure between about 2 and 80 bar.

18. A process as claimed in claim 1 further comprising the presence of an aprotic solvent.

19. A process for the production of esters comprising reacting acetylenically unsaturated compounds in the presence of a nucleophilic compound selected from the group consisting of butanol and methanol and a catalyst system comprising:

(a) a platinum (II) compound
(b) a bis-diarylphosphine of the formula $R_1R_2PRPR_3R_4$ (I) wherein $R_1,R_2,R_3$ and $R_4$ independently are selected from the group consisting of unsubstituted and substituted aryl groups selected from the group consisting of napthyl and phenyl groups, R is a trimethylene group; and
(c) a source of anions selected from the group consisting of sulphonic acid and sulphonic acid derivatives.

20. A process for producing acrylates comprising reacting acetylenically unsaturated compounds selected from the group consisting of substituted and unsubstituted ethyne and propyne, in the presence of a nucleophilic compound selected from the group consisting of butanol and methanol, at a temperature between about 50° and 200° C., at a pressure between about 2 and 80 bar in the presence of an etheric solvent and a catalyst system comprising:

(a) a platinum (II) compound,
(b) a phosphino compound selected from the group consisting of 1,3-bis(diphenylphosphino) propane, 1,4-bis(diphenylphosphino) butane, 1,3-bis(diethylphosphino) propane, 1,3-bis(di-2-cyanoethylphosphino) propane, and 1,3-bis(di-isopropylphosphino) propane; and
(c) an anion source selected from the group consisting of tertiary butylsulphonic acid and trifluoro acetic acid.

* * * * *